United States Patent [19]
Frantzen et al.

[11] Patent Number: 5,782,907
[45] Date of Patent: Jul. 21, 1998

[54] INVOLUTED SPRING STENT AND GRAFT ASSEMBLY AND METHOD OF USE

[75] Inventors: John J. Frantzen, Copperopolis; Peter S. Brown, Mountain View, both of Calif.

[73] Assignee: Devices for Vascular Intervention, Inc., Redwood City, Calif.

[21] Appl. No.: 501,771

[22] Filed: Jul. 13, 1995

[51] Int. Cl.$^6$ ...................................................... A61F 2/06
[52] U.S. Cl. ............................. 623/1; 606/108; 606/194
[58] Field of Search ........................... 623/1, 11, 12; 606/192, 194, 195, 108; 140/89; 29/227

[56] References Cited

U.S. PATENT DOCUMENTS

| | | |
|---|---|---|
| 3,657,744 | 4/1972 | Ersek . |
| 3,868,956 | 3/1975 | Alfidi et al. . |
| 4,512,338 | 4/1985 | Balko et al. . |
| 4,553,545 | 11/1985 | Maass et al. . |
| 4,560,374 | 12/1985 | Hammerslag . |

(List continued on next page.)

FOREIGN PATENT DOCUMENTS

| | | |
|---|---|---|
| 0 364 787 A1 | 4/1990 | European Pat. Off. . |
| 0 408 245 A1 | 1/1991 | European Pat. Off. . |
| 0 416 662 A2 | 3/1991 | European Pat. Off. . |
| 0 493 788 A1 | 12/1991 | European Pat. Off. . |
| 0 505 686 A1 | 1/1992 | European Pat. Off. . |
| 364045 A1 | 6/1987 | Germany . |
| 57-89859 | 6/1982 | Japan . |
| 2 135 585 | 9/1984 | United Kingdom . |
| WO 89/03232 | 4/1989 | WIPO . |
| WO 89/08433 | 9/1989 | WIPO . |
| WO 90/01969 | 3/1990 | WIPO . |
| WO 90/04982 | 5/1990 | WIPO . |
| WO 90/06094 | 6/1990 | WIPO . |
| WO 91/17744 | 11/1991 | WIPO . |
| WO 92/10218 | 6/1992 | WIPO . |

OTHER PUBLICATIONS

Wright et al.: Percutaneous Endovascular Stents: An Experimental Evaluation, 69–72, 1985, *Radiology Journal*.
Dotter: Transluminal Expandable Nitinol Coil Stent Grafting: Preliminary Report, pp. 259–260, Apr. 1983, *Radiology Journal*.
Cragg et al.: Non–Surgical Placement of Arterial Endoprostheses: A New Technique Using Nitinol Wire, pp. 261–263, Apr. 1983, *Radiology Journal*.
Dotter, Charles T.: Transluminally Placed Coilspring Endarterial Tube Grafts, pp. 329–332, Sep. 10, 1969, *Investigative Radiology*.
C.R. Bard: PE Plus Peripheral Balloon Dilatation Catheter, Aug. 1985, *CR Bard, Inc.*
Duprat et al.: Flexible Balloon–Expanded Stent for Small Vessels, pp. 276–278, 1987, *Radiology Journal*.
Maass et al.: Radiological Follow–up of Transluminally Inserted Vascular Endoprostheses: An Experimental Study Using Expanding Spirals, pp. 659–663, 1984, *Radiology Journal*.
Palmaz et al.: Expandable Intraluminal Graft: A Preliminary Study, pp. 73–77, 1985, *Radiology Journal*.

*Primary Examiner*—John G. Weiss
*Assistant Examiner*—Bruce E. Snow
*Attorney, Agent, or Firm*—Fulwider Patton Lee & Utecht, LLP

[57] ABSTRACT

An apparatus and method for forming or shaping an intraluminal stent for low profile delivery into a body lumen. A nickel titanium intraluminal stent has a tubular member formed from a plurality of coils which are bent to form lobe-shaped members, like a cloverleaf, to reduce the profile of the tubular member and form an involuted spring stent. The involuted spring stent will transform to the implanted diameter of the tubular member when exposed to body heat. The involuted spring stent can be attached to a tubular graft, or coated with a polymeric material to form an involuted spring graft, both of which can be used to repair aortic aneurysms.

4 Claims, 10 Drawing Sheets

U.S. PATENT DOCUMENTS

| | | |
|---|---|---|
| 4,580,568 | 4/1986 | Gianturco . |
| 4,655,771 | 4/1987 | Wallsten . |
| 4,733,665 | 3/1988 | Palmaz . |
| 4,739,762 | 4/1988 | Palmaz . |
| 4,740,207 | 4/1988 | Kreamer . |
| 4,762,128 | 8/1988 | Rosenbluth . |
| 4,776,337 | 10/1988 | Palmaz . |
| 4,795,458 | 1/1989 | Regan . |
| 4,800,882 | 1/1989 | Gianturco . |
| 4,830,003 | 5/1989 | Wolff et al. . |
| 4,856,516 | 8/1989 | Hillstead . |
| 4,877,030 | 10/1989 | Beck et al. . |
| 4,878,906 | 11/1989 | Lindemann et al. . |
| 4,886,062 | 12/1989 | Wiktor . |
| 4,893,623 | 1/1990 | Rosenbluth . |
| 4,907,336 | 3/1990 | Gianturco . |
| 4,913,141 | 4/1990 | Hillstead . |
| 4,921,479 | 5/1990 | Grayzel . |
| 4,922,905 | 5/1990 | Strecker . |
| 4,950,227 | 8/1990 | Savin et al. . |
| 4,969,458 | 11/1990 | Wiktor . |
| 4,969,890 | 11/1990 | Sugita et al. . |
| 4,986,831 | 1/1991 | King et al. . |
| 4,994,071 | 2/1991 | MacGregor . |
| 4,998,539 | 3/1991 | Delsanti . |
| 5,002,560 | 3/1991 | Machold et al. . |
| 5,007,926 | 4/1991 | Derbyshire . |
| 5,015,253 | 5/1991 | MacGregor . |
| 5,019,085 | 5/1991 | Hillstead . |
| 5,019,090 | 5/1991 | Pinchuk . |
| 5,026,377 | 6/1991 | Burton et al. . |
| 5,034,001 | 7/1991 | Garrison et al. . |
| 5,035,706 | 7/1991 | Gianturco et al. . |
| 5,037,392 | 8/1991 | Hillstead . |
| 5,037,427 | 8/1991 | Harada et al. . |
| 5,059,211 | 10/1991 | Stack et al. . |
| 5,061,275 | 10/1991 | Wallsten et al. . |
| 5,062,829 | 11/1991 | Pryor et al. . |
| 5,064,435 | 11/1991 | Porter . |
| 5,078,726 | 1/1992 | Kreamer . |
| 5,078,736 | 1/1992 | Behl . |
| 5,084,065 | 1/1992 | Weldon et al. . |
| 5,092,877 | 3/1992 | Pinchuk et al. . |
| 5,100,429 | 3/1992 | Sinofsky et al. . |
| 5,102,417 | 4/1992 | Palmaz . |
| 5,104,404 | 4/1992 | Wolff . |
| 5,108,416 | 4/1992 | Ryan et al. . |
| 5,116,318 | 5/1992 | Hillstead . |
| 5,116,365 | 5/1992 | Hillstead . |
| 5,122,154 | 6/1992 | Rhodes . |
| 5,123,917 | 6/1992 | Lee . |
| 5,133,732 | 7/1992 | Wiktor . |
| 5,135,536 | 8/1992 | Hillstead . |
| 5,158,548 | 10/1992 | Lau . |
| 5,161,547 | 11/1992 | Tower . |
| 5,163,958 | 11/1992 | Pinchuk . |
| 5,171,262 | 12/1992 | MacGregor . |
| 5,183,085 | 2/1993 | Timmermans . |
| 5,192,297 | 3/1993 | Hull . |
| 5,192,307 | 3/1993 | Wall . |
| 5,195,984 | 3/1993 | Schatz . |
| 5,197,978 | 3/1993 | Hess . |
| 5,290,295 | 3/1994 | Querals et al. . |
| 5,312,339 | 5/1994 | Boussignac et al. . |
| 5,507,771 | 4/1996 | Gianturco ................................ 623/1 |
| 5,549,663 | 8/1996 | Cottone, Jr. ............................. 623/1 |

INVOLUTED SPRING STENT AND GRAFT ASSEMBLY AND METHOD OF USE

BACKGROUND OF THE INVENTION

1. Field of the Invention

The present invention generally relates to endoprosthesis devices, including intraluminal vascular grafts, generally referred to as stents, adapted to be implanted in a body lumen, such as coronary arteries or to repair aortic aneurysms. More particularly, stents can be attached to a vascular graft to attach the graft to the aortic wall in the treatment of aortic aneurysms.

2. Description of Related Art

In expandable stents that are delivered with expandable catheters, such as balloon catheters, the stents are positioned over the balloon portion of the catheter and are expanded from a reduced diameter to an enlarged diameter greater than or equal to the diameter of the arterial wall by inflating the balloon. Stents of this type can be expanded to an enlarged diameter by deforming the stent by radially expanding it into engagement with the arterial wall. Other stents are self-expanding, through the properties of the materials constituting the stent or by design. Examples of intravascular stents can be found in U.S. Pat. Nos. 5,292,331 (Boneau); 4,776,337 (Palmaz); 4,580,568 (Gianturco); 4,856,516 (Hillstead); and 5,092,877 (Pinchuk), which are incorporated herein by reference in their entirety. These patents by no means make up the entire body of prior art relating to stents or vascular grafts, and are referred to herein by example only.

In typical balloon angioplasty procedures, a guiding catheter having a preformed distal tip is percutaneously introduced through the femoral artery into the cardiovascular system of a patient in a conventional Seldinger technique and advanced within the cardiovascular system until the distal tip of the guiding catheter is seated in the ostium of a desired coronary artery. A guidewire is positioned within an inner lumen of a dilatation catheter and then both are advanced through the guiding catheter to the distal end thereof. The guidewire is first advanced out of the distal end of the guiding catheter into the patient's coronary vasculature until the distal end of the guidewire crosses a lesion to be dilated, then the dilatation catheter having an inflatable balloon on the distal portion thereof is advanced into the patient's coronary artery over the previously introduced guidewire until the balloon of the dilatation catheter is properly positioned across the lesion. Once in a position across the lesion, the balloon, which is made of relatively inelastic materials, is inflated to a predetermined size with radiopaque liquid at relatively high pressure (e.g., greater than 4 atmospheres) to compress the arteriosclerotic plaque of the lesion against the inside of the artery wall and to otherwise expand the inner lumen of the artery. The balloon is then deflated so that blood flow can be resumed through the dilated artery and the dilatation catheter can be removed therefrom. Further details of dilatation catheters, guidewires, and devices associated therewith for angioplasty procedures can be found in U.S. Pat. Nos. 4,323,071 (Simpson-Robert); 4,439,185 (Lindquist); 4,516,972 (Samson); 4,538,622 (Samson et al.); 4,554,929 (Samson et al.); 4,616,652 (Simpson); 4,638,805 (Powell); and 4,748,982 (Horzewski et al.) which are hereby incorporated herein in their entirety by reference thereto.

A major problem which can occur during balloon angioplasty procedures is the formation of intimal flaps which can collapse and occlude the artery when the balloon is deflated at the end of the angioplasty procedure. Another characteristic of balloon angioplasty procedures is the large number of patients which are subject to restenosis in the treated artery. In the case of restenosis, the treated artery may again be subjected to balloon angioplasty or to other treatments such as by-pass surgery, if additional balloon angioplasty procedures are not warranted. However, in the event of a partial or total occlusion of a coronary artery by the collapse of a dissected arterial lining after the balloon is deflated, the patient may require immediate medical attention, particularly in the coronary arteries.

A major focus of recent development work in the treatment of heart disease has been directed to endoprosthetic devices called stents. Stents are generally cylindrically-shaped intravascular devices which are placed within an injured or damaged artery to hold it open. The device can be used to prevent restenosis and to maintain the patency of a blood vessel immediately after intravascular treatments. In some circumstances, they can also be used as the primary treatment device where they are expanded to dilate a stenosis and then left in place.

Two basic methods and systems have been developed for delivering stents to desired locations within body lumens. One method and system involves compressing or otherwise reducing the diameter of an expandable stent, disposing the compressed stent within a lumen provided in the distal end of a tubular catheter, advancing the catheter through the patient's vasculature until the distal end of the catheter is immediately adjacent to the desired vascular location and then pushing the stent out the distal end of the catheter into the desired location. Once out of the catheter, the compressed stent expands or is expanded to thereby hold open the artery or other body lument into which it is placed.

Another method and system involves disposing a compressed or otherwise small diameter stent about an expandable member such as a balloon on the distal end of a catheter, advancing the catheter through the patient's vascular system until the stent is in the desired location within a blood vessel and then expanding the expandable member on the catheter to expand the stent within the blood vessel. The expanded expandable member is then contracted and the catheter withdrawn, leaving the expanded stent within the blood vessel, holding open the passageway thereof.

The following references illustrate various types of stents and stent delivery systems. The list is meant to be exemplary, not exhaustive on the subject.

| U.S. 3,868,956 | U.S. 4,733,665 | U.S. 4,856,516 |
| --- | --- | --- |
| U.S. 4,503,569 | U.S. 4,760,849 | U.S. 4,878,906 |
| U.S. 4,512,338 | U.S. 4,762,128 | U.S. 4,886,062 |
| U.S. 4,553,545 | U.S. 4,768,507 | U.S. 4,907,336 |
| U.S. 4,560,374 | U.S. 4,795,458 | U.S. 4,913,141 |
| U.S. 4,655,771 | U.S. 4,800,882 | U.S. 4,923,464 |
| U.S. 4,665,918 | U.S. 4,830,003 | U.S. 4,950,227 |

Another area in which stents are useful is in attaching a tubular graft to the walls of the aorta to repair an aortic aneurysm.

An abdominal aortic aneurysm ("AAA") is an abnormal dilation of the arterial wall of the aorta in the region of the aorta that passes through the abdominal cavity. The condition most commonly results from atherosclerotic disease. Frequently, abdominal aortic aneurysms are dissecting aneurysms that are formed when there is a tear or fissure in the arterial lining or wall through which blood is forced and where it eventually clots, forming a thrombosis that swells and weakens the vessel. Abdominal aortic aneurysms do not cause pain, but are easily detected in a thorough physical examination. If the aneurysm is not detected and treated, it is likely to rupture and cause massive hemorrhaging fatal to the patient.

Treatment of AAAs typically takes the form of arterial reconstructive surgery. One such method is bypass surgery, in which an incision is made into the abdominal cavity, the aorta is closed off above and below the site of the aneurysm, the aneurysm is resected, and a synthetic graft or tube sized to approximate the diameter of the normal aorta is sutured to the vessel to replace the aneurysm and to allow blood flow through the aorta to be reestablished. The graft commonly is fabricated of a biocompatible material that is compliant and thin-walled. Nylons and synthetic fibers such as those manufactured under the trademarks DACRON or TEFLON have been found to be suitable for the construction of the graft. Studies have shown that the mortality rate associate with this surgical procedure is favorable (less than 5%) when it is performed prior to rupture of an aneurysm. However, patients having an AAA are typically over 65 year of age, and often have other chronic illnesses which increase the risk of perioperative or post-operative complications. Those patients thus are not ideal candidates for this type of major surgery. Further, it has been pointed out that this procedure is not often successfully resorted to after an aneurysm has ruptured (the mortality rate increases to over 65%) because of the extensiveness of the surgery and the time required to prepare a patient for it.

Another procedure developed as an alternative to conventional surgical methods involves placement of a graft at the site of the aneurysm. However, the graft is deployed there by being routed through the vascular system carried by a catheter, wire or other device suitable for negotiating the vasculature. The graft and its deployment system often are introduced into the blood stream percutaneously with a femoral approach and the entire procedure can be performed using local rather than general anesthesia. Once the graft has been positioned at the aneurysm, it is disengaged from the delivery system and can be affixed to the aortic wall both distally and proximally of the aneurysm. For this purpose, grafting systems usually include fixation means such as staples or hooks which can be manipulated and driven into the intima of the vessel via some mechanical feature of the system, or by some physical process, such as expansion of the graft through application of pressure or temperature change. To avoid premature detachment of the graft and to prevent the attachment elements from damaging the vessels or halting the forward movement of the system while the graft is being routed to the treatment site, the systems often are provided with a feature such as a capsule or a sheath that protects and contains the graft until such time as deployment is desired.

Once the graft is in place, it is positioned in the vessel spanning the site of the aneurysm such that the walls of the graft are generally parallel to the walls of the affected area of the aorta. The aneurysm thus is excluded from the circulatory system by the graft rather than being resected altogether.

Grafting systems are known that include what is commonly referred to as an attachment system for deploying the graft. The attachment system is typically a tubular device which is fitted inside and is generally coaxial with the graft, and can extend beyond either or both of the proximal and distal ends of the graft. The attachment system often has a latticelike or open weave structure, which provides it with flexibility and which promotes rapid endothelial tissue growth through the structure once the graft has been deployed. It may be provided with additional hook-like elements for penetration of the intimal walls for attachment of the graft to the aorta, or those hook-like elements may be provided on the graft itself. Graft systems of the type described can be found in U.S. Pat. Nos. 4,787,899; 4,104, 399; 5,219,355; and 5,275,622, which are incorporated herein by reference.

The actual function of delivering the graft may be accomplished by inflating a balloon of a catheter by introducing pressurized fluid into a lumen of the catheter from a source external to the patient. Inflation of the balloon applies a force to the graft and any attachment system (i.e., a stent) supplied therein which extends radially and presses the graft and attachment system into the vessel wall just above and just below the aneurysm. When an attachment system is used, disengagement of the catheter from the graft also has been accomplished by taking advantage of the chemical properties of the material from which the attachment system is manufactured. For example, a prior art attachment system may be in the form of a coil of a nickel-titanium alloy, available under the trademark "NITINOL," that will expand radially upon being heated to a higher temperature. The longitudinal dimension of any attachment system used must account for any reduction in length that might result from radial expansion of the device. Other devices used to attach a graft to the aortic wall for AAA repair include intravascular stents of the type found in U.S. Pat. No. 4,733,665.

In order for a stent to be used most advantageously in a coronary artery or with a graft deployment system for treatment and repair of aneurysms, it is desirable for the stent to be composed of a biocompatible material, and to be simultaneously flexible enough to comply with the catheter or other element used to route through the often tortuous vascular path to the site of the aneurysm or a lesion and strong enough radially to maintain patency of the artery once delivered. The stent should be well suited to deployment by a delivery system that is not overly complex, and is reliable and easy to operate. Although various graft delivery systems have been proposed, none adequately provides all of the desirable features.

What has been needed and has heretofore unavailable is a stent and stent and graft assembly which has a good degree of flexibility for efficient advancement through tortuous passageways, and which has a very low profile for delivery purposes, yet can expand to a relatively large diameter for implantation purposes. The present invention meets these needs.

SUMMARY OF THE INVENTION

An intraluminal stent is transformed from a tubular-shaped member having an implantable diameter sized to approximate the inside diameter of a body lumen, to a low profile delivery diameter for intraluminal delivery through a patient's body lumen. More specifically, the stent has a tubular member with a distal end and a proximal end and the tubular member has a first implanted diameter defined by a plurality of coils. The first implanted diameter is slightly larger than the inside diameter of the vessel in which the stent is implanted. The coils of the tubular member are bent and shaped into lobe-shaped members, such as cloverleaf-shaped members which form an involuted spring stent. The involuted spring stent has a delivery diameter which is a smaller diameter than the implanted diameter of the tubular member. The low profile delivery diameter allows the involuted spring stent to be transported through a patient's body lumen until it reaches the site where it is to be implanted. Upon exposure to body heat, the involuted spring stent, which can be formed of a shaped-memory alloy such as nickel titanium (NiTi), transforms back to the tubular member configuration having the implanted diameter. Thus, the coils of the tubular member expand to the implanted diameter and the stent is thereby attached to the vessel wall where it is permanently implanted.

The involuted spring stent can be inserted in a sheath so that it can be delivered transluminally into a body lumen with the sheath protecting the body lumen from the stent. In one embodiment of the invention, the involuted spring stent is inserted into a sheath by winding it upon a rotating screw, with the sheath surrounding the involuted spring stent. The sheath helps to retain the stent in its delivery diameter configuration as well as protecting the body lumen from the stent. Once the stent is transported intraluminally to the site of implantation, the rotating screw can be counter-rotated so that the involuted spring stent unwinds and is exposed to body heat, whereupon it transforms into the tubular member as described above.

Preferably, the tubular member is formed from a metallic ribbon having a rectangular cross-section. It also can be formed from a metallic wire having a circular cross-section.

In an alternative embodiment, the tubular member has at least one longitudinal support rib which extends substantially from the distal end to the proximal end of the tubular member to add support to the tubular member.

In one embodiment of the invention, the stent is coated with a polymer, such as polyurethane, so that it forms a tubular graft that is a fluid-tight conduit. The inside of the stent can be coated with Teflon® so that blood will more easily flow through the tubular graft with less likelihood of turbulence. After coating the stent, it is bent in much the same manner described above so that it forms a plurality of lobes to form an involuted spring stent having a low profile intraluminal delivery diameter. Since the polyurethane and Teflon® coatings are thin and somewhat pliant, the coatings conform to the bends in the stent. Thus, a coated involuted spring graft is formed for implanting in a body lumen. In one particular application, the coated involuted spring graft is implanted in an aorta so that it spans an aortic aneurysm. To implant the stent, the bent coils of the coated involuted spring graft return to their normal shape and expand outwardly to press against the aortic wall to implant the coated graft. Blood will flow through the coated graft which has formed a fluid-tight seal proximal and distal to the aneurysm so no blood can flow into the aneurysm.

In another embodiment of the invention, the stent of the present invention is attached to a tubular graft for repairing aortic aneurysms, or other aneurysms in various other body passageways. The tubular graft, which is not expandable, must be folded along its length in order to reduce its delivery profile. More particularly, at least a portion of the stent is attached to the tubular graft by bonding, suturing or by incorporating the stent into the graft matrix. Preferably, the stent is attached to the tubular graft after the stent has been bent to form an involuted spring stent so that the stent and the tubular graft have a very low profile and delivery diameter as described above. The stent and-graft assembly are formed into the lobe-shaped members described above for the stent alone, with the graft being folded along its length. The involuted spring stent and attached tubular graft can be inserted in a sheath so that the low profile delivery diameter can be maintained, and to protect the vessel walls from the stent and the tubular graft.

Once the tubular graft is positioned in an aorta so that the graft spans the aneurysm, the sheath is withdrawn so that the involuted spring stent and the tubular graft are deployed in the aorta. As described above, the patient's body heat will cause the shaped-memory alloy of the stent to quickly transform and expand the coils so that the stent returns to its tubular configuration having the implanted diameter. As the stent expands, the tubular graft unfolds to its implanted diameter. The stent is sized so that its implantable diameter is slightly larger than the inside diameter of the healthy aorta above the aneurysm so that the stent presses firmly into healthy aortic tissue.

These and other aspects and advantages will become apparent from the following detailed description, and the accompanying drawings, which illustrate by way of example the features of the invention.

DETAILED DESCRIPTION OF THE PREFERRED EMBODIMENTS

The stent of the present invention is depicted in FIGS. 1–17 for use in various body lumens, including use in repairing coronary arteries and combining the stent with a tubular graft to repair aortic aneurysms. The stent of the present invention, however, is not limited to the coronary arteries or for repairing aortic aneurysms, but can be used on other body lumens as well.

Figures 1, 2:
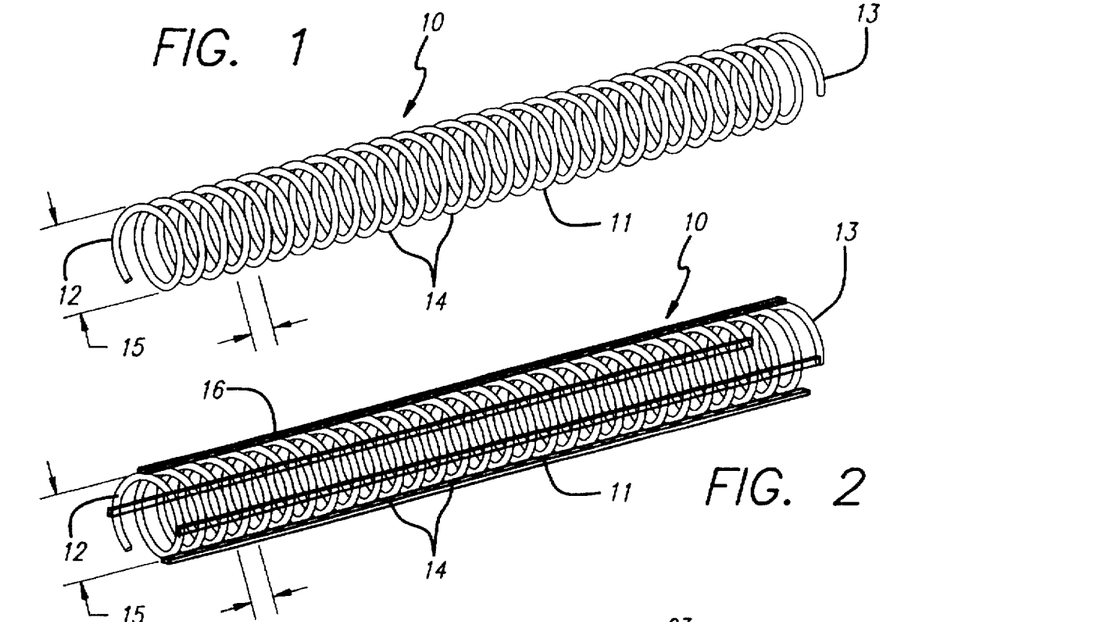
FIG. 1 is a perspective view depicting the stent of the present invention having its implantable diameter configuration.
FIG. 2 is a perspective view depicting the stent of FIG. 1 having longitudinal support ribs which provide extra support and rigidity to the stent in order to maintain the patency of a body lumen.

Referring to FIG. 1, in one preferred embodiment stent 10 is formed from tubular member 11 which has a distal end 12 and proximal end 13. The wall surface of tubular member 11 is defined by coils 14, which can be helical coils. In the configuration of the invention shown particularly in FIG. 1, coils 14 have an implanted diameter 15 that is sized to fit within a body lumen in which stent 10 is implanted. In other words, the maximum diameter of stent 10 is intended to be the same as or slightly larger than the inside diameter of the body lumen in which it is implanted. Due to its construction and material properties, as will be described more fully herein, stent 10 is biased outwardly so that it can exert a slight outward pressure to insure that it firmly attaches to a body lumen.

In an alternative form of the invention, as depicted in FIG. 2, stent 10 is formed from a tubular member 11 having longitudinal support ribs 16 which run substantially the entire length of the tubular member. Longitudinal support ribs 16 are intended to provide more rigidity to stent 10 and to lend support so that coils 14 have less of a tendency to separate or flex after stent 10 has been implanted. For example, the blood pressure in the aorta can reach 100 mmHg. In order to add rigidity and insure that stent 10 remains firmly implanted, longitudinal support ribs 16 are incorporated along the surface of tubular member 11 so that coils 14 do not separate due to the high blood flow pressure.

Figure 3:
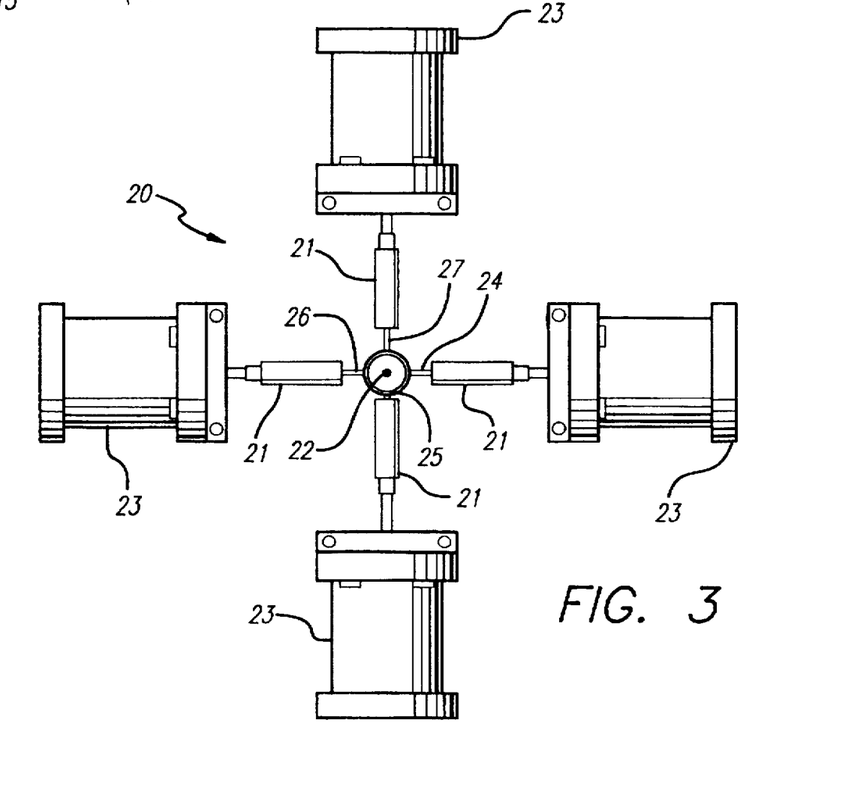
FIG. 3 is a top view depicting a lobe forming fixture which transforms the stent of FIG. 1 into an involuted spring stent as depicted in FIG. 4.
Figure 4:
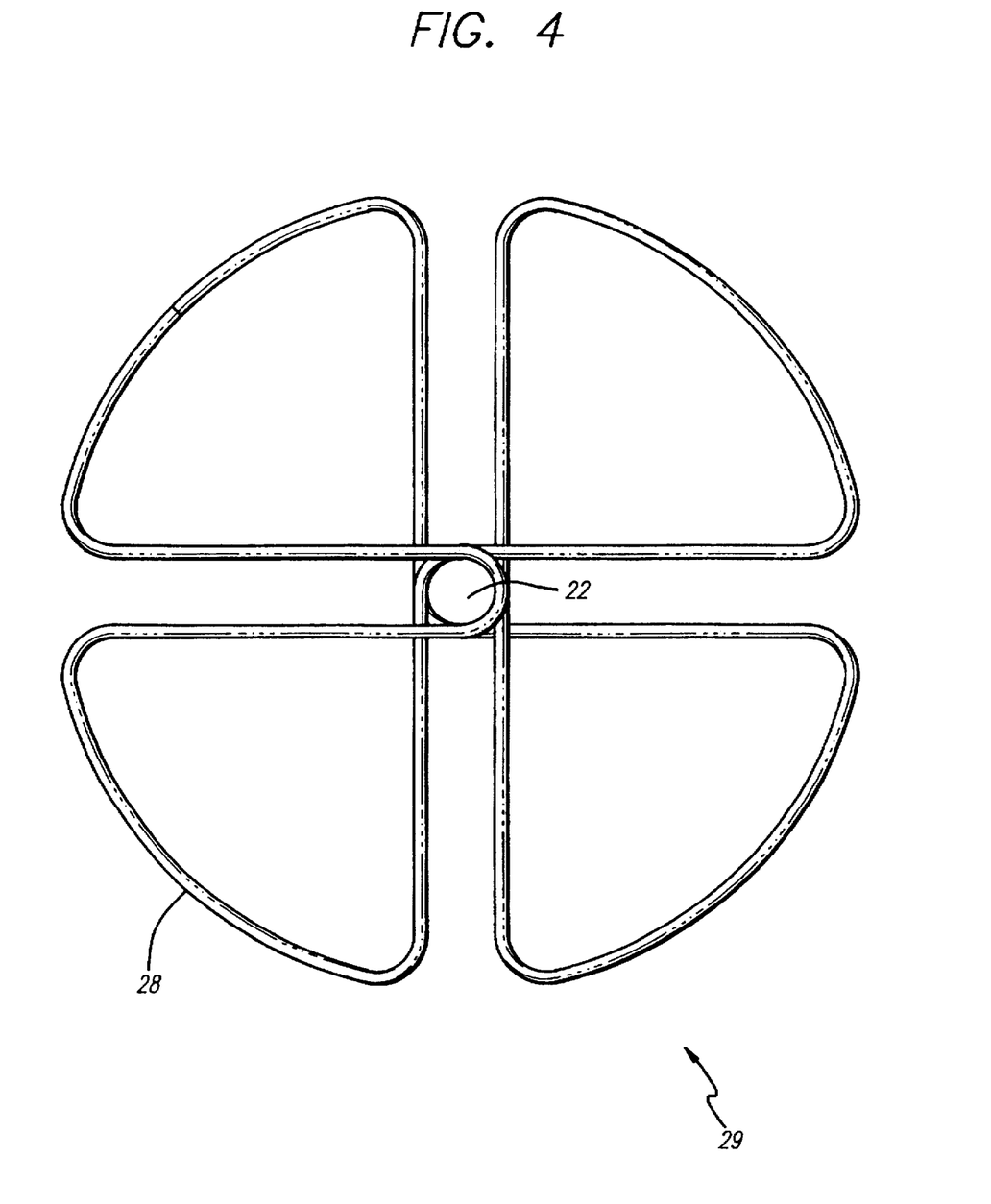
FIG. 4 is a view looking down the longitudinal axis of FIG. 1 where the stent is being transformed into a cloverleaf-shaped structure to form an involuted spring stent.
Figure 5:
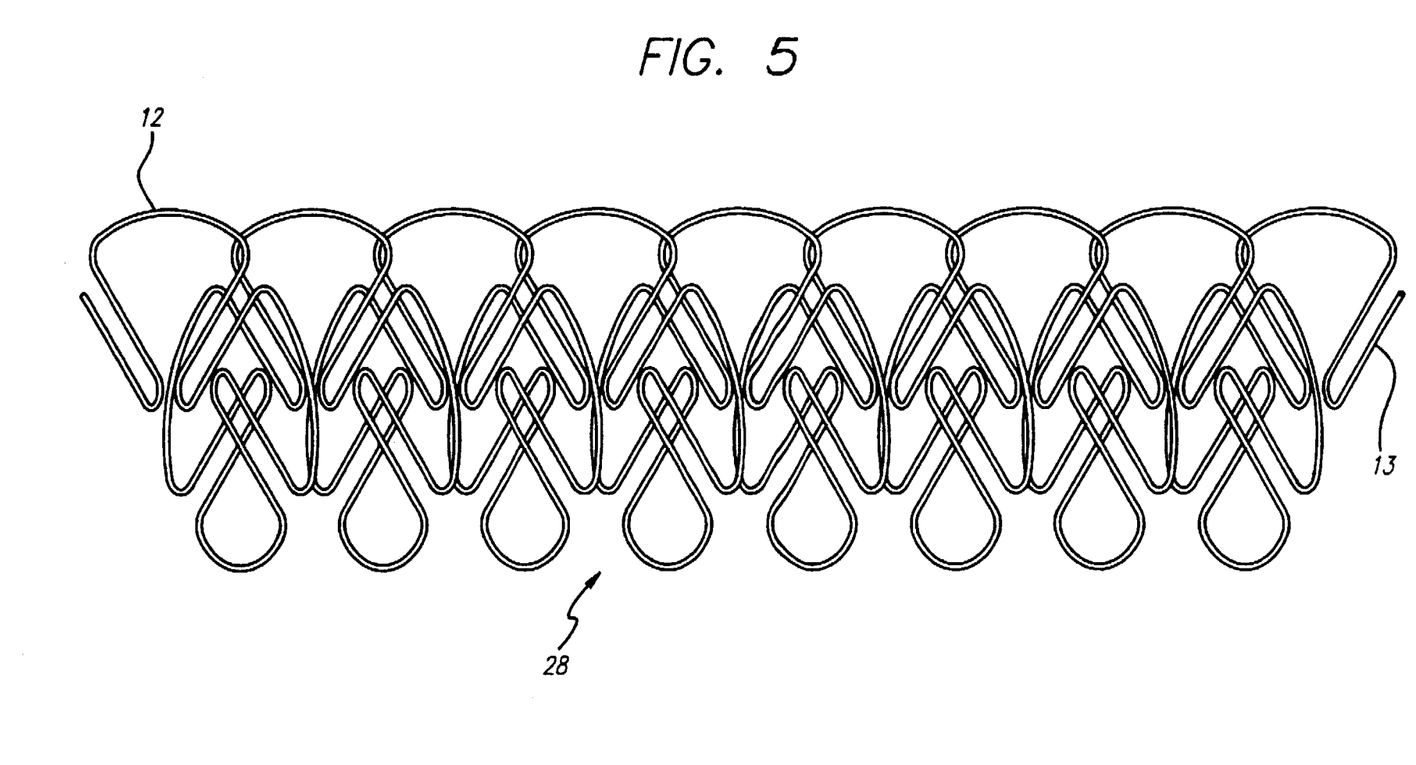
FIG. 5 is a side view depicting the involuted spring stent.

In keeping with the invention, the preferred method of reducing the profile of stent 10 is depicted in FIGS. 3–5. As seen in FIG. 3, a four-lobe-forming fixture 20 is used to bend and reshape tubular member 11 to reduce its profile so that it may be delivered intraluminally. Four-lobe-forming fixture 20 is comprised of a cylinder 21 and a mandrel 22 and four drive units 23.

In order to bend and reshape tubular member 11, it is inserted, with mandrel 22, within proximal contact of the four cylinders 21 and their respective drive units 23 running through tubular member 11 as it is reshaped. Each of drive units 23 are respectively equipped with first pin 24, second pin 25, third pin 26 and fourth pin 27. These pins are used to bend the coils 14 of tubular member 11 inwardly toward mandrel 22 as shown in FIG. 4. By way of example, first pin 24 is fully extended and bending one of coils 14 inwardly so that it can be retained in its bent and inward position by mandrel 22. Thereafter, first pin 24 is retracted and second pin 25 is extended into contact with another of the coils 14 so that the coil is bend inwardly and retained by mandrel 22. Second pin 25 is then retracted and third pin 26 is extended into contact with the coils. As can be seen in FIG. 4, the procedure continues until all of the coils have been bent inwardly to form an involuted spring stent 28 having a cloverleaf-shaped configuration 29. FIG. 5 depicts the involuted spring stent 28 from a side view, with mandrel 22 removed for clarity purposes.

As is clear from FIGS. 4 and 5, involuted spring stent has a low profile delivery diameter 30 that is substantially smaller than implanted diameter 15 of tubular member 11 while four-lobe-forming fixture 20 is depicted as a preferred method of bending coils 14, other devices are contemplated as are differing numbers of lobes (i.e., three-lobe or five-lobe stents).

Stent 10 of the present invention preferably is made of shaped-memory alloy, preferably nickel-titanium shape-memory alloy, which has a martinsitic metallurgical state and austenitic metallurgical state, and a transition temperature therebetween. Shape-memory alloys are known in the art and are discussed in Shape-Memory Alloys, *Scientific American*, Volume 281, pages 74–82 (November 1979), incorporated herein by reference.

Shape-memory alloys undergo a transition between an austenitic state and a martinsitic state at certain temperatures. When they deformed while in the martinsitic state they will retain this deformation as long as they are retained in this state, but will revert to their original configuration when they are heated to a transition temperature, at which time they transform to their austenitic state. The temperatures at which these transitions occur are affected by the nature of the alloy and the condition of the material. Nickel-titanium-based alloys (NiTi), wherein the transition temperature is slightly lower than body temperature, are preferred for the present invention. It is desirable to have the transition temperature set at just below body temperature to insure a rapid transition from the martinsitic state to the austenitic state when stent 10 is implanted in a body lumen.

As described with respect to FIGS. 3–5, tubular member 11 is in an austenitic metallurgical state, and is deformed or shaped by four-lobe-forming fixture 20 while in its martinsitic metallurgical state to form involuted spring stent 28. Involuted spring stent 28 will remain in its cloverleaf-shaped configuration 29 as long as the temperature to which it is exposed remains somewhat below body temperature (approximately 98° F.). Involuted spring stent 28 will rapidly transform back to tubular member 11 to form stent 10 when it is exposed to body temperatures, which should approach 98° F.

In order to enhance the attachment capabilities of tubular member 11, it is preferred that it be formed from a metallic ribbon of NiTi. It is further preferred that the metallic ribbon have a rectangular cross-section so that the edges of coils 14 have a tendency to dig into the body lumen in which stent 10 is implanted. Other cross-sectional shapes for the coils 14 of tubular member 11 are contemplated, such as a round wire or a square metallic ribbon.

Figure 6:
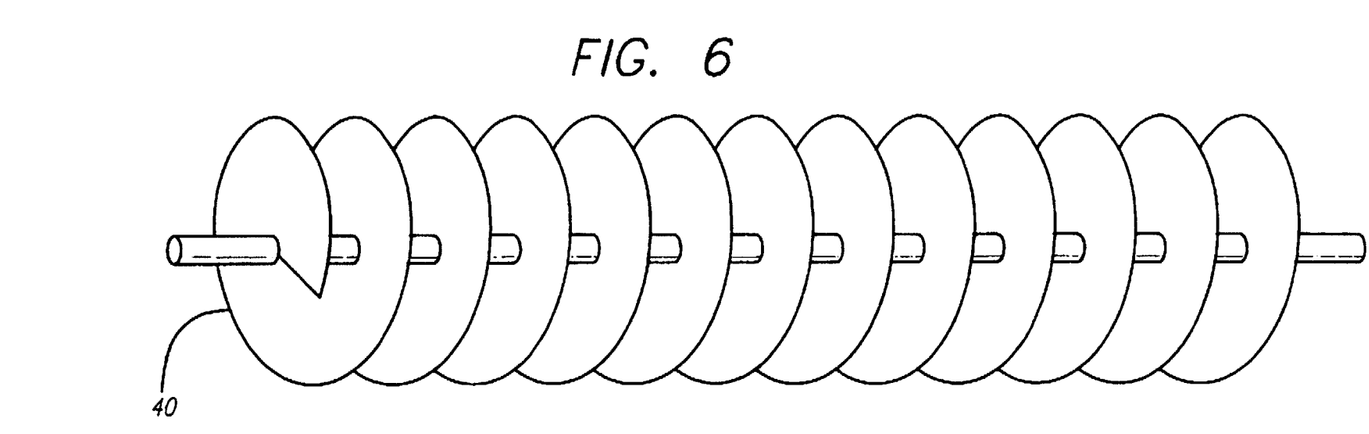
FIG. 6 is a side view depicting a screw used to wind the involuted spring stent of FIG. 5.
Figure 7:
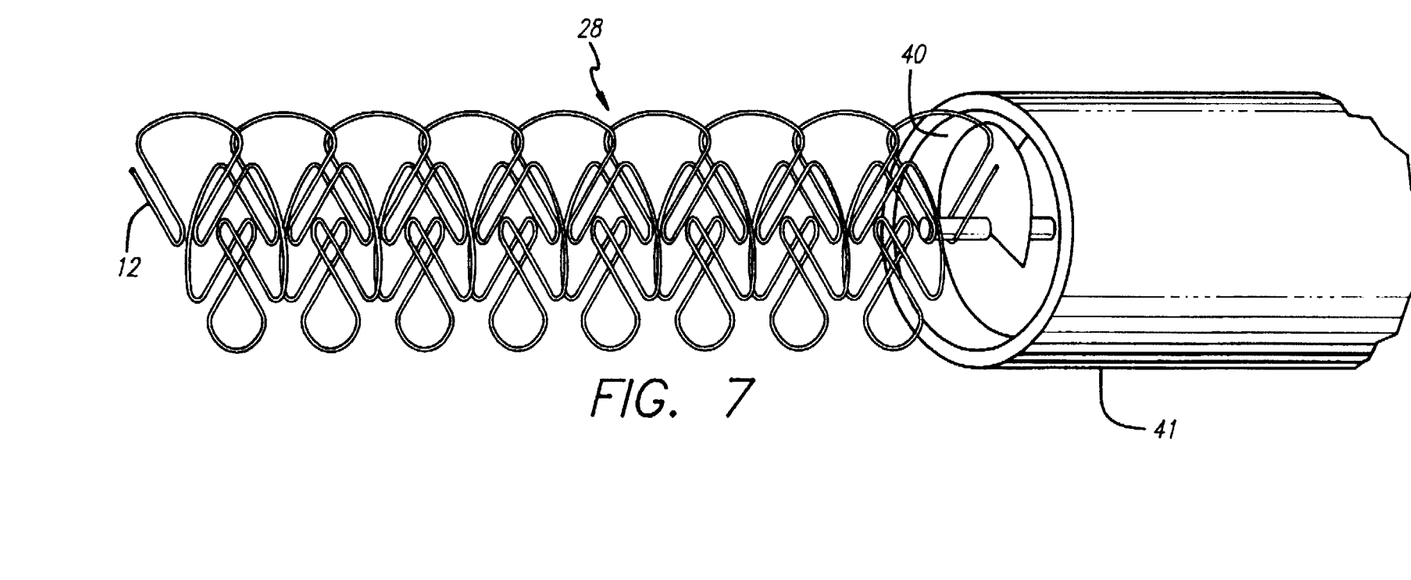
FIG. 7 is a side view depicting a portion of the involuted spring stent being wound onto the rotating screw of FIG. 6 and being inserted or drawn into a sheath to assist in retaining the involuted spring stent in its delivery diameter configuration.

One example of how stent 10 is used in a body lumen is depicted in FIGS. 7–10. Referring to FIGS. 6 and 7, involuted spring stent 28 is wound on a rotating screw 40 so that it fits within sheath 41. Sheath 41 is mounted on a catheter (not shown) for intraluminal delivery, for example, by a femoral approach which is well known in the art. Involuted spring stent 28 is transported intraluminally inside sheath 10 so that it does not uncoil, and to protect the vessel walls from any sharp edges on the stent.

Figure 8:
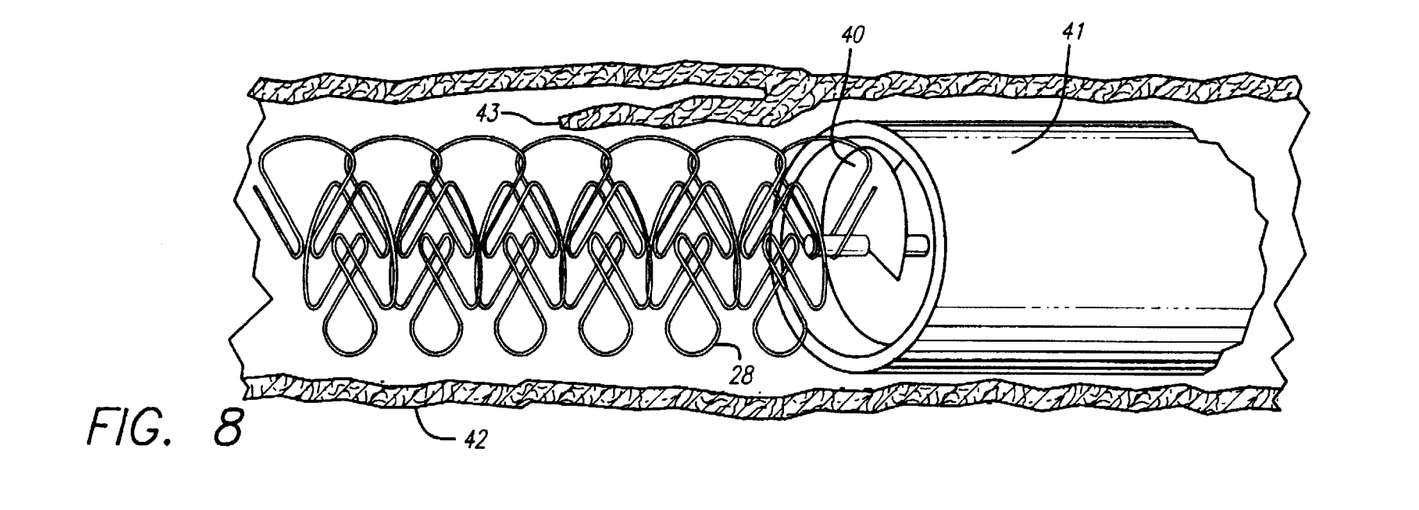
FIG. 8 is a partial cross-sectional view of the involuted spring stent being ejected from the sheath for implantation in an artery.
Figure 9:
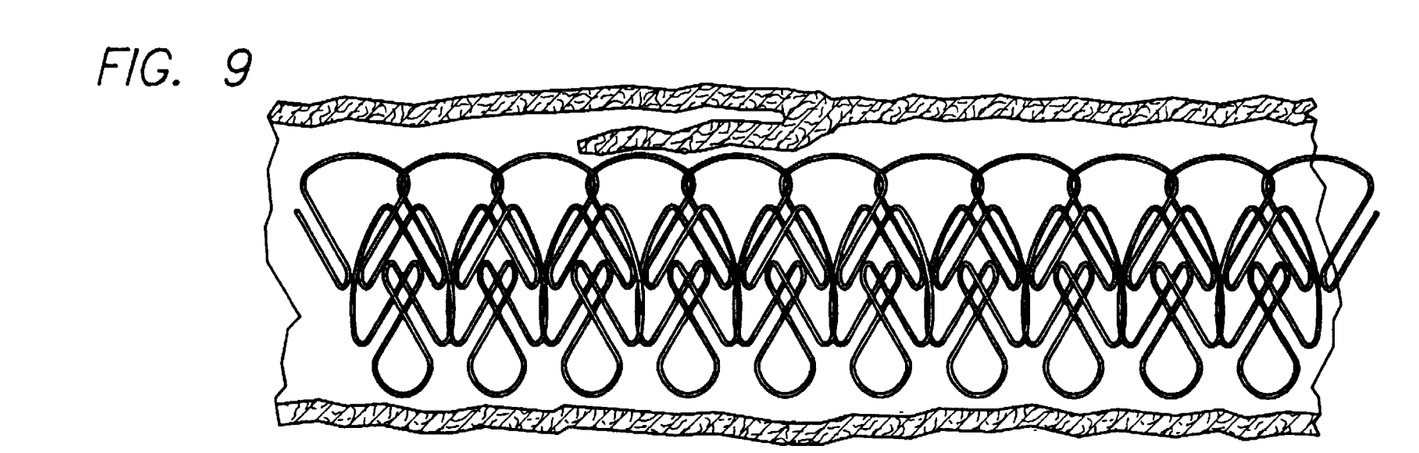
FIG. 9 is a cross-sectional view of the involuted spring stent in a coronary artery before it is heated and transformed to the tubular member configuration of FIG. 10.
Figure 10:
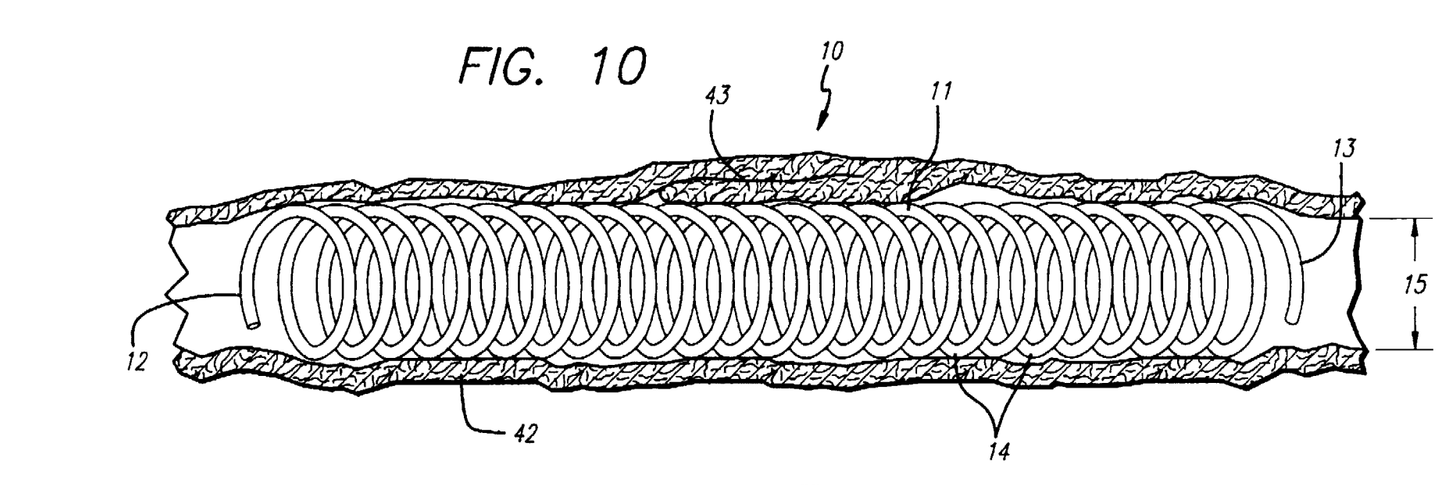
FIG. 10 is a cross-sectional view of the tubular member after it has transformed from the involuted spring stent of FIG. 9, wherein the stent has expanded to its implanted diameter.

As depicted in FIG. 8, once the catheter has positioned sheath 41 at the site where it will be implanted, such as at a dissection or intimal flap 43 in coronary artery 42, rotating screw 40 is counter-rotated so that involuted spring stent 28 is ejected from sheath 41. Immediately upon contact with the higher temperature in coronary artery 42, involuted spring stent 28 expands as seen in FIG. 9. As it approaches the transition temperature, the stent will transform from its martinsitic state (the involuted spring stent 28) to its austenitic state forming tubular member 11. Thus, as seen in FIGS. 9 and 10, involuted spring stent 28 transforms into tubular member 11 when it reaches its transition temperature. In the process, tubular member 11 will hold open coronary artery 42, and will tack up intimal flap 43 so that it does not obstruct blood flow in the artery.

Other means are contemplated to deliver involuted spring stent 28 in a body lumen. For example, although not shown, involuted spring stent can be mounted on a mandrill running through the stent, similar to mandrel 22 as shown in FIG. 4. The mandrel will assist in holding involuted spring stent 28 in its cloverleaf-shaped configuration. With the mandrel through its center, involuted spring stent can be inserted in a sheath, such as sheath 41, but without using a rotating screw. The involuted spring stent can then be delivered intraluminally as described and ejected and deployed by removing the mandrel.

In another preferred embodiment, as shown in FIGS. 11–14, stent 10 is coated with a polymeric material and implanted to span and repair an aortic aneurysm. Stent 10 is comprised of coated tubular member 45 having a plurality of coils 46 that have a thin and flexible coating 47 on their outer surface 48. Coating 47 can be any suitable polymer that is fluid-impermeable and biocompatible. One such polymer, polyurethane, can be applied to outer surface 48 of coils 46 by dipping tubular member 45 into the polyurethane. The thickness of coating 47 will depend upon the application, but it should be thin enough so it does not interfere with bending coils 46 as will be described. Also, to ensure non-turbulent blood flow through tubular member 45, a thin and flexible Teflon® coating 49 is applied to the inner surface 48A of coils 46.

Coated tubular member 45 can now have its implanted diameter 15 reduced to a delivery diameter 30 in the same manner as described for tubular member 11 shown in FIGS. 1, 3 and 4. Since polyurethane coating 47 and Teflon® coating 49 are thin and flexible, the coatings will fold as the lobes are formed by bending coils 46. The result is an involuted spring graft 50, as shown in FIG. 13, which can be used to repair an aneurysm, such as aortic aneurysm 51, as shown in FIG. 14.

Figures 11, 12, 14:
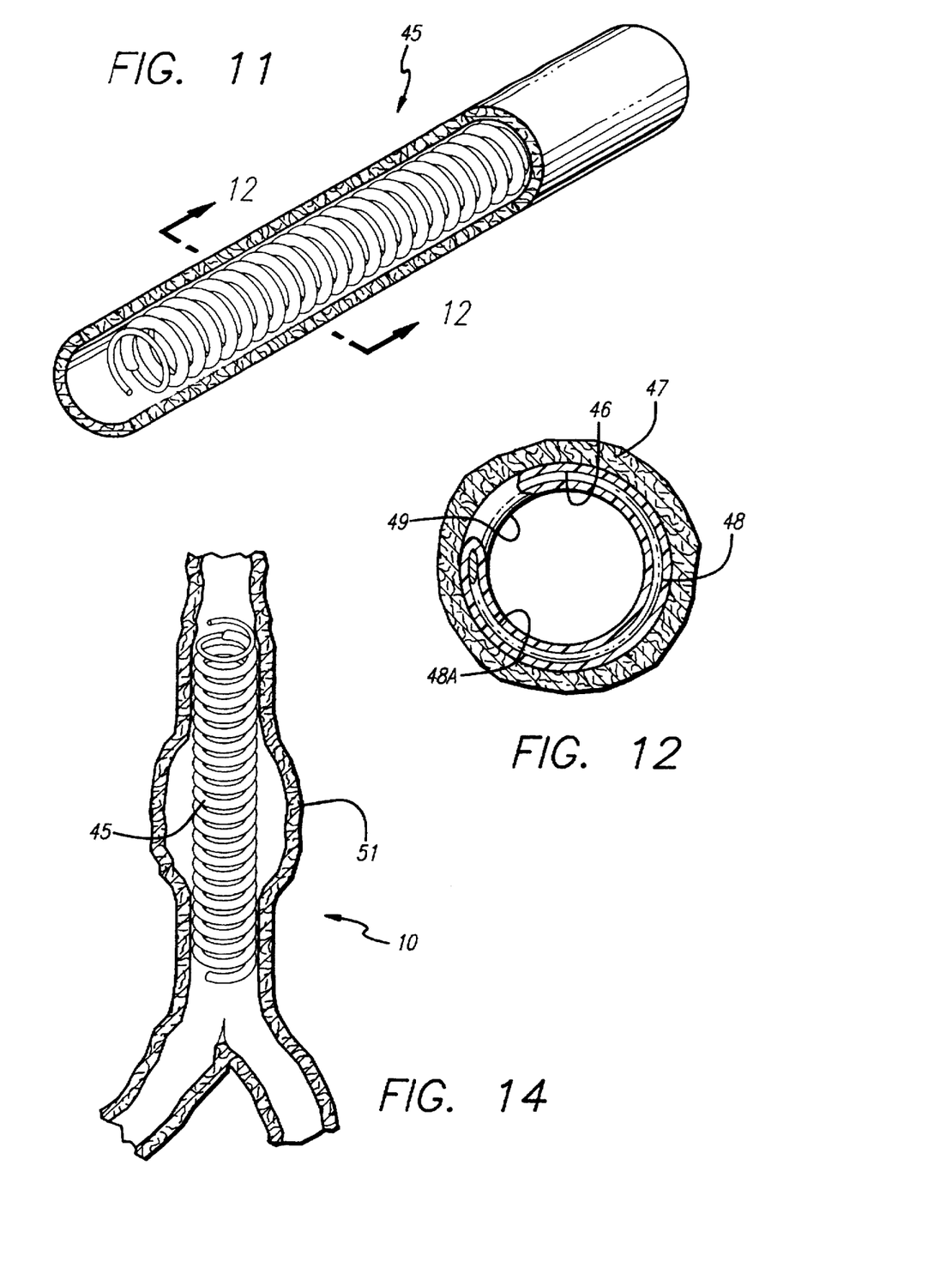
FIG. 11 is a perspective view of an intraluminal stent having a polymeric coating on its outer surface and its inner surface.
FIG. 12 is a cross-sectional view taken along lines 12—12 of FIG. 11 depicting the tubular member having a polymeric coating on its inner surface and its outer surface.
FIG. 14 is a partial cross-sectional view depicting he tubular member having a polymeric coating on its inner surface and outer surface and fully expanded on its implanted diameter, so that it is in contact with the aortic wall so as to preclude blood flow into an aortic aneurysm.
Figure 13:
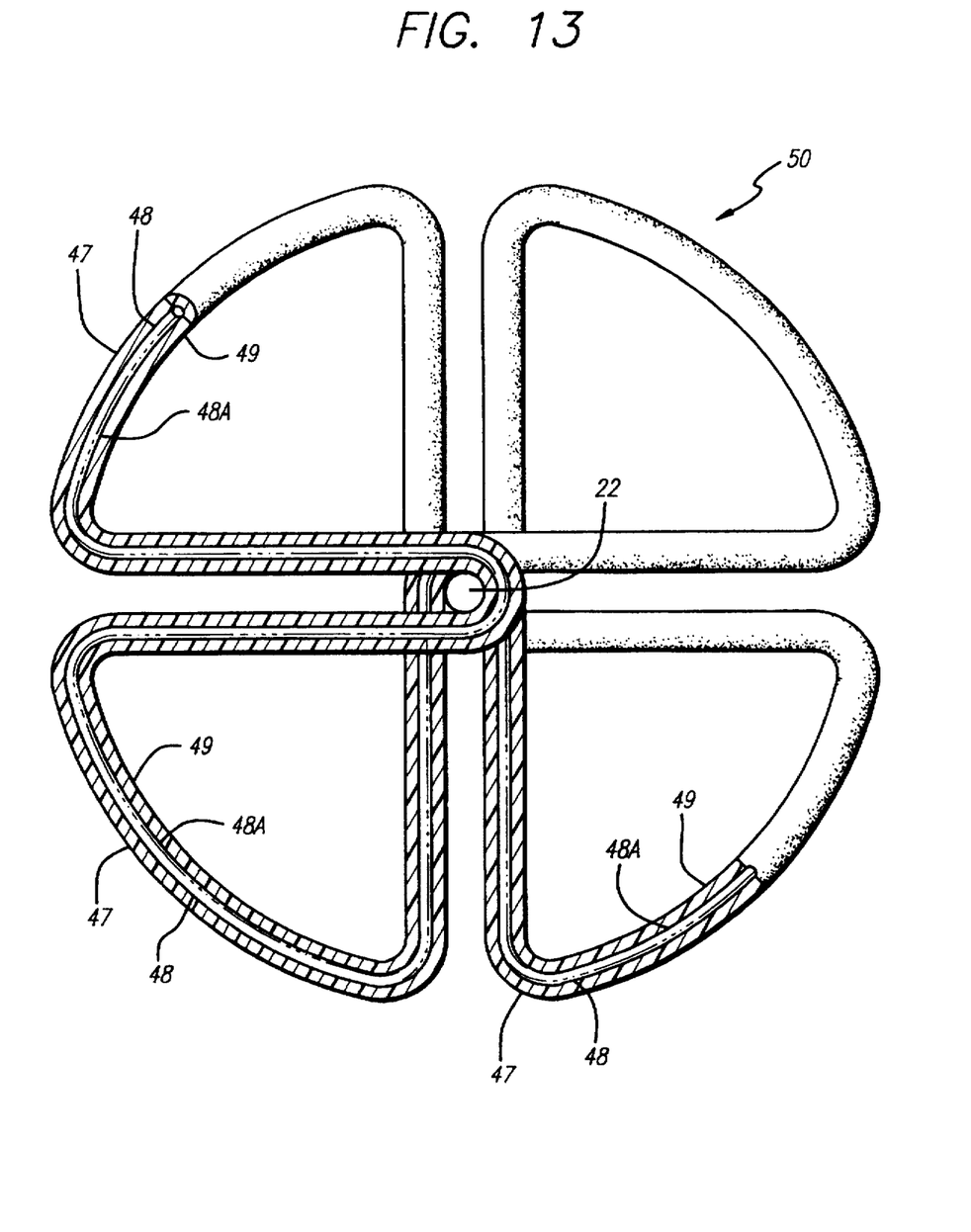
FIG. 13 is a cross-sectional view of an involuted spring graft having polymeric coatings on its inner surface and outer surface, with four lobes formed in the coils of the stent portion of the graft.

As shown in FIGS. 13–14, involuted spring graft 50, having a reduced profile delivery diameter 30, is implanted to span aortic aneurysm 51. The involuted spring graft 50 can be delivered intraluminally in a sheath until it is deployed. In keeping with the invention, coated tubular member 45 is formed from a NiTi material as described and when involuted spring graft 50 is exposed to body heat, it transforms to tubular member 45 and presses against the aortic wall to firmly implant across aneurysm 51. Tubular member 45 forms a fluid-tight seal with the aorta so that no blood flows into aneurysm 51. As involuted spring graft 50 transforms into coated tubular member 45, polyurethane coating 47 and Teflon® coating 49 unfold since they are flexible.

While preferred coatings of polyurethane and Teflon® have been referenced, it is contemplated that other polymers also are suitable for use with stent 10. Further, it may be desirable to coat only a portion of stent 10 with a polymer, leaving distal end 12 and proximal end 13 uncoated so that the ends will contact the aortic wall for a more positive attachment means.

Figure 15:
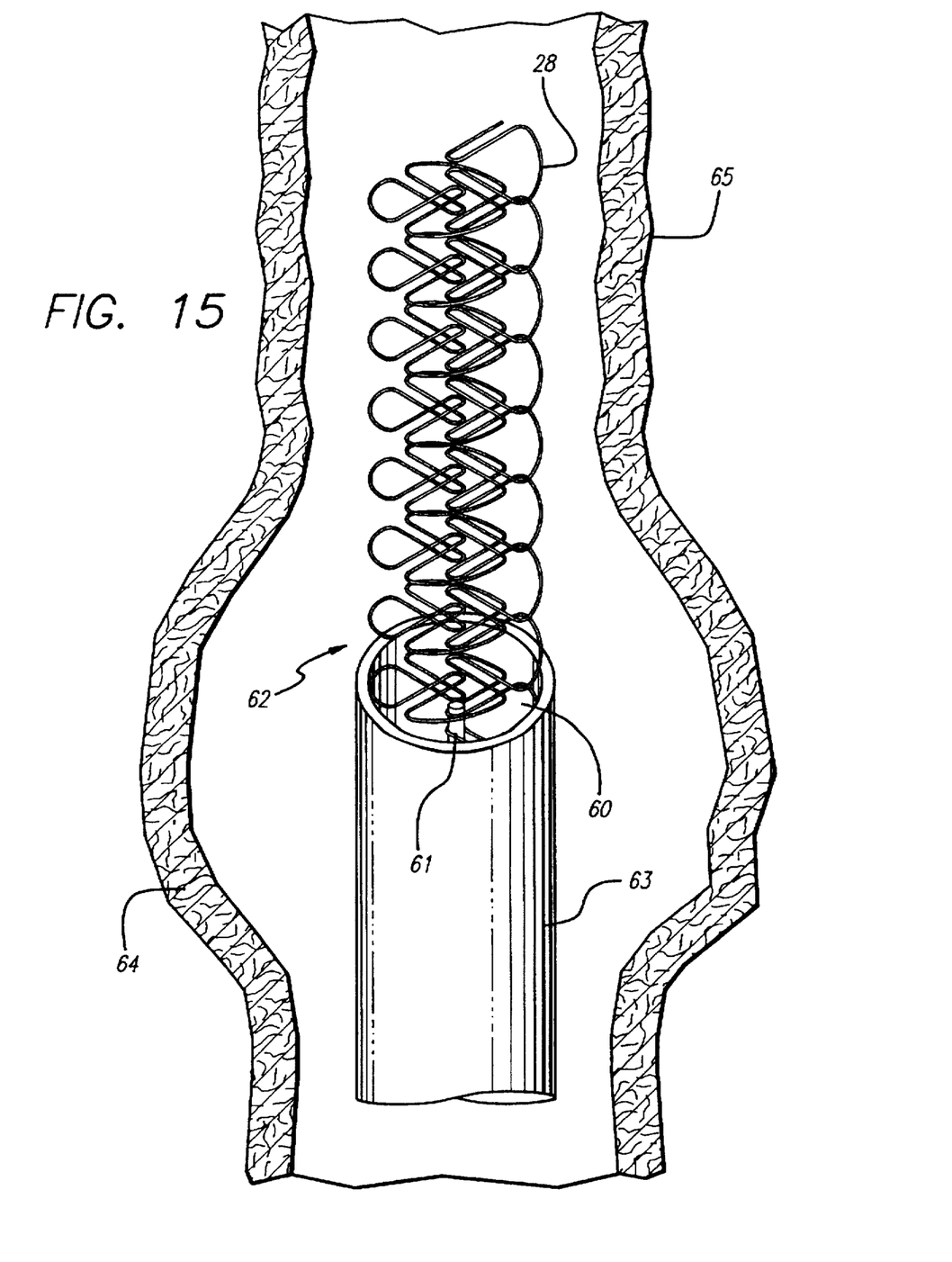
FIG. 15 is a partial cross-sectional view depicting an involuted spring stent attached to a tubular graft as the graft and stent assembly is being ejected from a sheath for implantation in the aorta to repair an aortic aneurysm.
Figure 16:
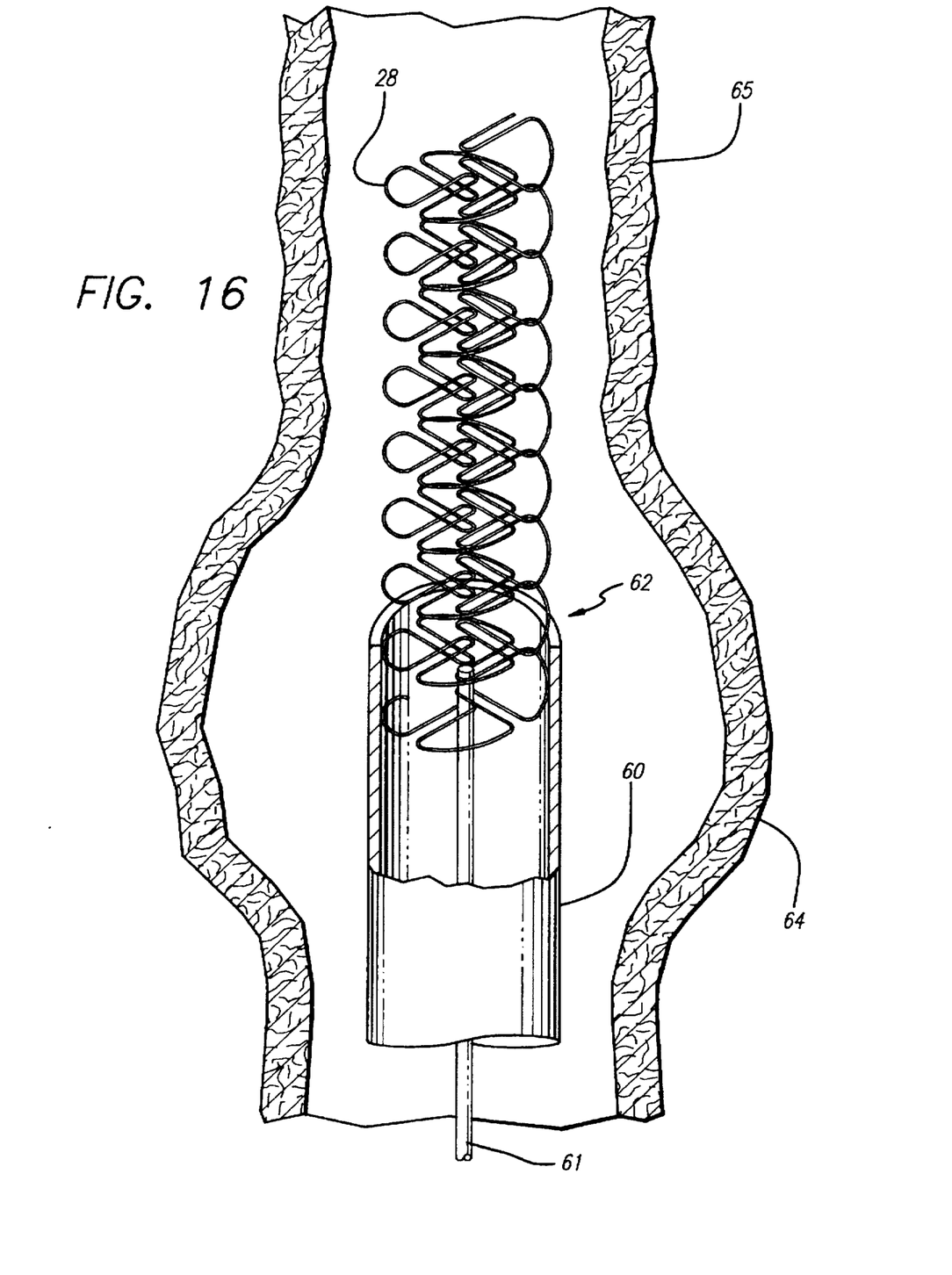
FIG. 16 is a partial cross-sectional view depicting an involuted spring stent attached to a tubular graft prior to the stent and graft expanding into contact with the aortic wall.
Figure 17:
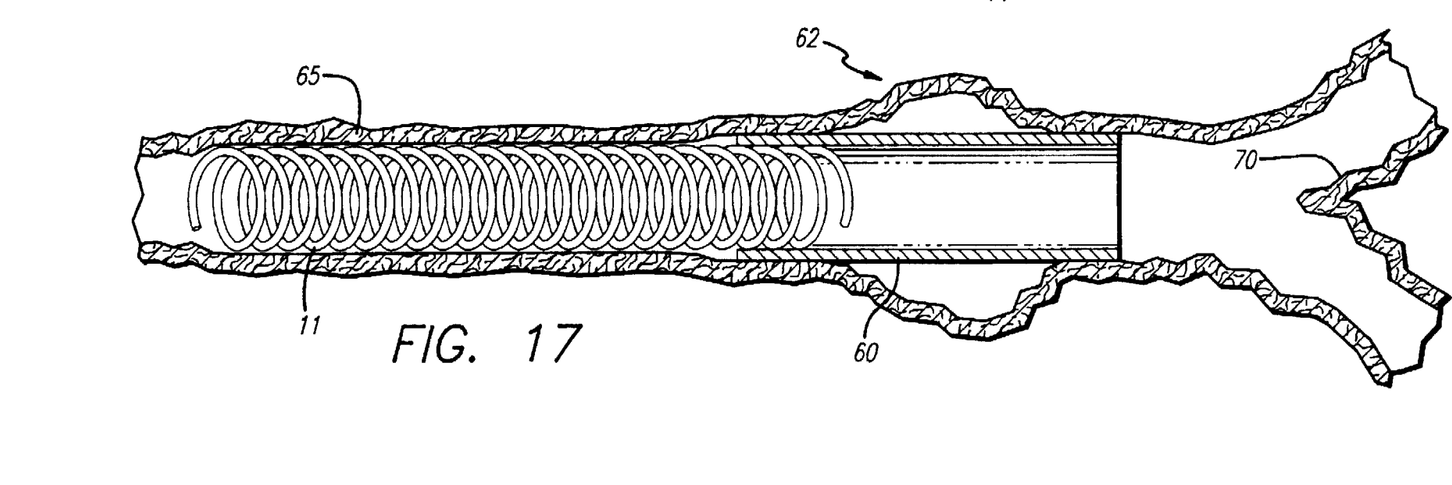
FIG. 17 is a partial cross-sectional view depicting the graft and stent assembly fully expanded into its implanted diameter and in contact with the aortic wall to preclude blood flow into the aneurysm.

In another preferred embodiment, as depicted in FIGS. 15–17, stent 10 is attached to a tubular graft for repairing, for example, an abdominal aneurysm. In this embodiment, involuted spring stent 28 is attached to tubular graft 60. At least a portion of involuted spring stent is attached to at least a portion of tubular graft 60 by bonding, for example with adhesives, or by suturing the stent to the graft. Tubular graft 60 will have at least four folds 61 that correspond to the cloverleaf-shaped configuration 29 of involuted spring stent 28. Since the stent and tubular graft have the same general cloverleaf-shaped configuration, they present a very low profile for intraluminal delivery, as seen in FIGS. 15 and 16. Once the stent and tubular graft are attached, they form graft and stent assembly 62 which is intended to remain a permanent attachment. The tubular member can be made from DACRON™ or TEFLON™, or similar materials which are known in the art and are known to be biocompatible. In order to implant graft and stent assembly 62 in the aorta, it is inserted in sheath 63 (FIG. 15) and transported intraluminally, generally by a femoral approach. When the involuted spring stent 28 is positioned above (distal) to the aneurysm 64, and with tubular graft 60 positioned to span aneurysm 64, graft and stent assembly 62 is ejected from sheath 63. Graft and stent assembly 62 can be pushed distally out of sheath 63 by a pusher rod (not shown) or sheath 63 can be withdrawn proximally by known means to expose graft and stent assembly 62.

FIGS. 16 and 17 depict graft and stent assembly 62 before and after it undergoes the transformation as described above. Involuted spring stent 28 will transform from its martinsitic state to its austenitic state upon reaching the transformation temperature, which is somewhat below body temperature. It is contemplated that the transformation occur rapidly, even as involuted spring stent 28 is being ejected from sheath 63. As seen in FIG. 17, stent 10 has transformed into tubular member 11 and has expanded radially outwardly to its implanted diameter 15 so that it presses firmly up against aortic wall 65. Graft and stent assembly 62 is sized so that it approximately matches the inner diameter of aortic wall 65. With respect to tubular member 11, it is generally sized so that its implanted diameter 15 is substantially the same or slightly larger than the inside diameter of aortic wall 65. It is important to provide a secure attachment for graft and stent assembly 62, and by sizing tubular member 11 to expand to an implanted diameter 15 that is slightly larger than the inside diameter of aortic wall 65, tubular member 11 will press firmly into aortic wall 65.

Referring to FIG. 17, while one embodiment of the invention has been described with respect to graft and stent assembly 62, aortic aneurysms often occur near or in the aortic bifurcation 70. When an aneurysm is near aortic bifurcation 70, a bifurcated graft (not shown) is implanted to repair the aneurysm and maintain patency of the body lumen. Bifurcated tubular grafts are known in the art, and the stent of the present invention can be used to attach the bifurcated graft to the aortic bifurcation in much the same manner as described for graft and stent assembly 62.

Further, although not shown, stent 10 can be attached to the proximal end of tubular graft 60 in order to more securely attach the proximal end of the graft to the aortic wall 65. It is generally left to the treating physician to determine whether stent 10 is to be attached to both the distal and proximal ends of tubular graft 60 to secure it to aortic wall.

Also not shown, is the use of stent 10, as depicted in FIG. 2, with longitudinal support ribs 16 in conjunction with tubular graft 60 to repair an aneurysm. It is contemplated that the longitudinal support ribs 16 would provide further support to a graft and stent assembly to repair an aneurysm.

While a particular form of the invention has been illustrated and described, it will also be apparent to those skilled in the art that various modifications can be made without departing from the spirit and scope of the invention. For example, a wide variety of materials will be adaptable for use in devices according to the present invention. It is not intended that the present invention be limited except by the appended claims.

What is claimed is:

1. A method of shaping and delivering an intraluminal stent for low profile delivery into a body lumen, the method comprising:

providing a tubular member having a distal end, a proximal end, and an implantable diameter formed by a plurality of helical coils;

reducing said implantable diameter of said tubular member by bending said helical coils into lobe-shaped members to form an involuted spring stent having a delivery diameter;

inserting said involuted spring stent into a sheath by providing a rotating screw within said sheath, and turning said screw to coil said involuted spring stent into said sheath;

delivering said sheath and said involuted spring stent intraluminally through the body lumen; and withdrawing said sheath proximally and implanting said involuted spring stent in the body lumen.

2. The method of shaping and delivering the intraluminal stent of claim 1, wherein said rotating screw is counter-rotated to force said involuted spring stent to uncoil and be ejected from said sheath.

3. The method of delivering and implanting a graft and stent assembly, including a tubular member having a distal end and a proximal end, said tubular member having a first implanted diameter defined by a plurality of coils, bending said coils of said tubular member into lobe-shaped members forming an involuted spring stent having a second delivery diameter, and a tubular graft having a first end and a second end, the method comprising:

attaching a portion of said first end of said stent to said first end of said graft to form a graft and stent assembly;

inserting said graft and stent assembly into a sheath mounted on a catheter by providing a rotating screw within said sheath to wind said involuted spring stent onto said rotating screw so that said involuted spring stent and said graft are retained by said sheath;

percutaneously inserting said catheter with said graft and stent assembly into a body lumen and intraluminally transporting said graft and stent assembly;

positioning said graft portion of said graft and stent assembly to span an aortic aneurysm;

withdrawing said sheath to expose said graft and stent assembly;

implanting said graft and stent assembly in the aorta; and withdrawing said sheath and said catheter from the body lumen.

4. The method of delivering and implanting the graft and stent assembly of claim 3, wherein said rotating screw is counter-rotated to force said involuted spring stent to unwind and be ejected along with said graft from said sheath.

* * * * *